United States Patent [19]

Bunce et al.

[11] Patent Number: 4,482,521
[45] Date of Patent: Nov. 13, 1984

[54] SUPPORT MEANS

[75] Inventors: Roger A. Bunce, Bourneville, England; Rolf O. Studer, Basel, Switzerland

[73] Assignee: The Secretary of State for Social Services in Her Britannic Majesty's Government of the United Kingdom of Great Gritain and Northern Ireland, London, United Kingdom

[21] Appl. No.: 265,709

[22] Filed: May 21, 1981

[51] Int. Cl.³ ................. G01N 33/54; G01N 33/48
[52] U.S. Cl. .................................. 422/102; 422/69; 422/73; 422/104; 436/809
[58] Field of Search ............... 422/102, 104, 311; 261/94, 95, 114; 55/379; 436/809

[56] References Cited

U.S. PATENT DOCUMENTS

| | | | |
|---|---|---|---|
| 3,034,869 | 5/1962 | Peterson | 422/311 |
| 3,702,238 | 11/1972 | Armistead et al. | 422/195 |
| 3,864,108 | 2/1975 | Brookman | 55/379 |
| 3,956,071 | 5/1976 | O'Brien | 196/46 |
| 4,089,664 | 5/1978 | Noland | 55/379 |
| 4,131,431 | 12/1978 | Siposs | 422/47 |
| 4,141,128 | 2/1979 | Wonderling | 55/379 |
| 4,184,894 | 3/1980 | Noland | 55/379 |
| 4,200,613 | 4/1980 | Alfrey et al. | 436/809 |
| 4,207,289 | 6/1980 | Weiss | 422/104 |
| 4,276,069 | 6/1981 | Miller | 55/379 |
| 4,336,035 | 6/1982 | Evenstad et al. | 55/379 |

Primary Examiner—Michael S. Marcus
Attorney, Agent, or Firm—Stevens, Davis, Miller & Mosher

[57] ABSTRACT

A support means for supporting more than six objects is disclosed. The support means comprises a substantially planar member having more than six siting means therein; and fixed thereto, one to each siting means, cage-like structures extending from said planar member substantially normal thereto, each cage-like structure being at least constricted at its end remote from said planar member; so that in use an object inserted in any one of said cage-like structures, and allowed to fall therein, is retained at the end thereof remote from said planar member. The planar member may be a substantially flat plate and each siting means a hole in said flat plate. The cage-like structure may, for example, be of helical form or of basket form.

11 Claims, 6 Drawing Figures

SUPPORT MEANS

BACKGROUND OF THE INVENTION

The present invention relates to supports for small objects, more especially, although not exclusively, plastics forms, e.g. spheres, which are coated for example with material to react, in a process of analysis, with biological fluids or solutions thereof.

Certain chemicals, for example the globulin fraction of antiserum against alpha-fetoprotein, may be absorbed or covalently bonded to solid phases such as the plastic polystyrene. This absorption or bonding is utilized in the determination of, for example, the concentration of alpha-fetoprotein in human blood serum. The testing procedures normally used have involved bringing the chemical and the solid phase onto which it is to be absorbed or covalently bonded into contact with each other manually. Typically, two different types of manual procedures have been used; either a plastics solid form has been dipped or immersed in the appropriate coating solution, or the inside surface of a plastics tube-like container has been coated by filling the container with the coating solution and then emptying. The coated forms may then be used to determine the concentration of an analyte in a sample. Each stage of this analysis has required a manual transfer which is time consuming, leads to poor precision, in measurement, causes problems in maintaining patient identity and is expensive.

Plastics forms have been supported, in solution for coating, washing, or reaction in analysis, by stems which in turn have been supported from above. From the point of view of expense and convenience in manufacture and packing, and, at least, of convenience in use, it is preferable to do away with such supporting stems and use, for example, a plain sphere as the plastics form.

It has been conventional in various industries, for coating, washing or draining of objects, to support them singly, or in numbers in a perforated container. However, the problems of chemical analysis to which, in particular, plastics forms are applied, requires minimal contact of the support means support with the plastics form. This minimal contact allows maximal circulation of fluid around the plastics form, and also maximal drainage on withdrawal from the fluid. It is also highly desirable that the plastics form be able to move in relation to the support. In medical work, in particular, maintenance of patient identity requires that each plastics form has its own individual support. The present invention meets these requirements to a very large extent and provides a means for supporting plastics forms so that they may easily be inserted into apparatus, used for analysis, and then removed from the apparatus.

SUMMARY OF THE INVENITON

According to the invention, support means for supporting more than six objects comprises a substantially planar member having more than six siting means therein; and fixed thereto, one to each siting means, cage-like structures extending from said planar member substantially normal thereto, each cage-like structure being at least constricted at its end remote from said planar member; so that in use an object inserted in any one of said cage-like structures, and allowed to fall therein, is retained at the end thereof remote from said planar member.

The planar member may be a substantially flat plate, each siting member then being a hole in said plate. Preferably each cage-like structure is tapered in diameter away from the planar member and may have the end thereof remote from said planar member conforming substantially in shape to that of a given object required to be supported in said cage-like structure.

Each cage-like structure is preferably a filament formed in at least one helix fixed at one end in a respective siting means and constricted at the end thereof remote from said planar member. The filament may be a metal wire, for example stainless steel, and may further be covered with a layer of inert material, for example polytetrafluoroethylene. The helix may be reinforced by an external shrunk-on or moulded sleeve.

The planar member may conveniently be provided with locating holes of characteristically unsymmetrical cross section to mate, in use, with pegs of a complementary shape on a coacting abutment. Alternatively, the planar member may have locating pegs of characteristically unsymmetrical cross section or arrangement to mate with holes of complementary shape in an abutment.

In a modified construction, each cage-like structure is a basket comprising a plurality of filaments extending from said planar member substantially normal thereto, and shaped at the end of the structure remote from said planar member so that, in use, an object inserted in such basket, and allowed to fall therein, is retained at the end thereof remote from said planar member. Each filament may be a metal wire, such as stainless steel, and can be coated with an inert material, for example polytetrafluoroethylene or a polyurethane varnish.

BRIEF DESCRIPTION OF THE DRAWINGS

The invention will be further described, by way of example only, with reference to the accompanying drawings, in which.

DETAILED DESCRIPTION OF THE INVENTION

Figure 1:
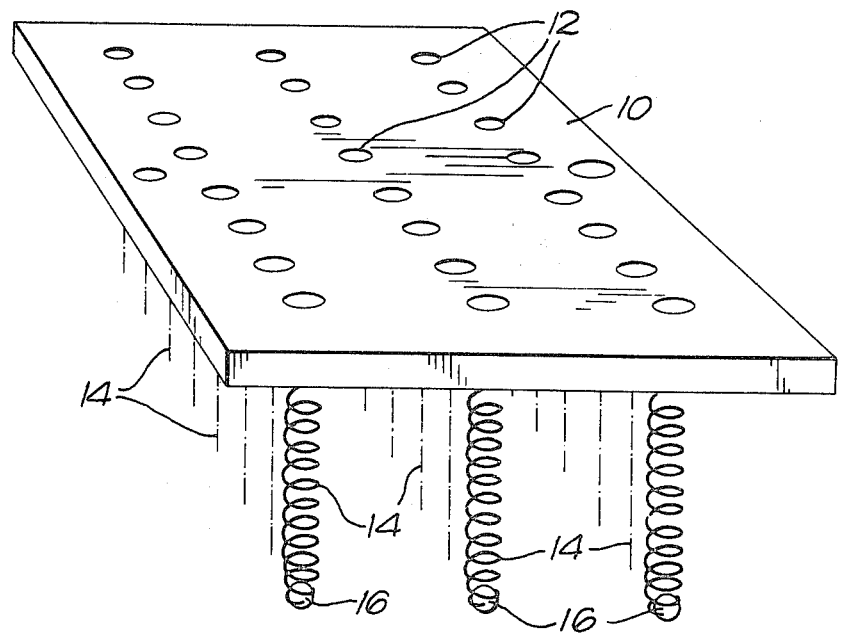
FIG. 1 is a trimetric general view of a support means according to the invention.
Figure 2:
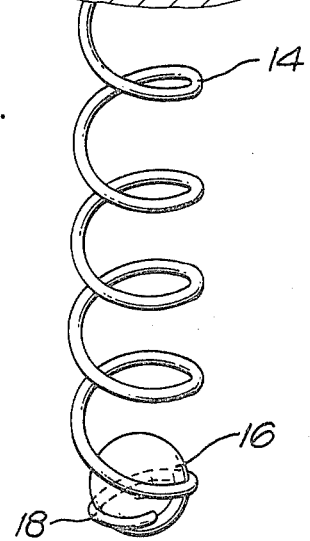
FIG. 2 is a scrap view of part of the support means on a larger scale.

The support means comprises as illustrated in FIG. 1, a planar member in the form of a flat plate 10 in which are a number of holes 12, of which, in this embodiment there are twenty four, although up to a hundred or more such holes may be provided. In this embodiment each hole 12 has a female thread, and each is provided with a helix 14, of which three only are shown in FIG. 1, to avoid complication of the drawing. The remaining helices are indicated diagrammatically by their center lines. Each complete helix is shown supporting a plastic solid form 16 of spherical shape. A form 16 is, in use, inserted through a hole 12 in the plate 10 and, (the plate being horizontal) falls to the end of the helix 14; that is to say the lower or remote end. FIG. 2 indicates how the plastics solid form 16 is prevented from dropping through the lower end of the helix. Substantially the last half turn at the lower end of the helix is constricted by being shaped, as indicated at 18, and turned inwards, slightly towards the axis of the helix. Alternatively, the last half turn may be bent in to a somewhat smaller radius or curvature than the remainder of the helix. In either case the plastics form 16 is permitted to rest loosely at the lower end of the helix, having minimal contact therewith.

In this embodiment of the invention, the filament from which the helices are made is basically stainless steel wire. In order to avoid reaction with fluids used in analysis, or in coating or washing the forms 16, the stainless steel wire is provided with an inert protective surface layer. For this purpose polyurethane varnish, and polytetrafluoroethylene have been found to be adequately effective. The protective layer may be provided as a thin-walled tube slid onto the wire and sealed at the lower end; or the wire may be sprayed with, or dipped in, the inert material which is then allowed to harden or set. Alternatively, a filament consisting wholly of suitably inert plastics material may be used.

Figure 3:
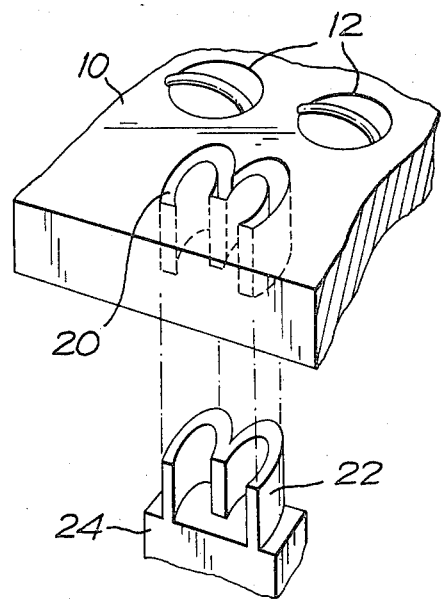
FIG. 3 is a scrap view of part of the support means showing locating means for locating the support means on an abutment.

Especially in analysis for medical diagnostic purposes, it may be very important to ensure patient identity between a particular plastics form 16, or set of such forms, and a or a set of containers of fluid of given composition. Maintenance of identity can be assisted by providing the plate 10 with locating holes 20 of characteristically unsymmetrical cross section, to mate with pegs 22 of complementary shape on a coacting abutment, as illustrated in FIG. 3. The abutment 24 may be part of an analysis apparatus. In an alternative construction, not separately illustrated, the peg 22 may be part of the plate 10 and the hole 20 part of the abutment 24.

Figure 4:
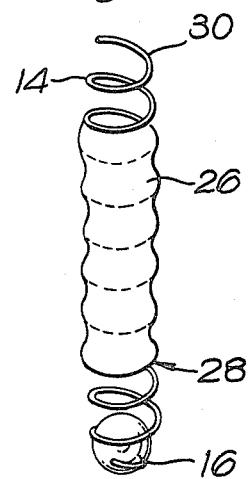
FIG. 4 illustrates one optional means for rendering a part of the support means less flexible by reinforcing it.

So that access of fluid to a plastics form 16 may be as free as possible, the filament of which the helices 14 are constructed should be of as small cross section as practicable. This small cross section may give a helix which is too flexible, and which responds too readily to, for example, currents of washing fluid; even to the extent of releasing the form 16 from the helix. It has been found that a helix made from a small cross section filament can be rendered less flexible by enclosing part of the length of the helix in a shrunk-on sleeve of heat shrinkable membrane, usually a plastics material, as illustrated in FIG. 4, at 26. The sleeve 26 is confined to that part of the helix (about ⅔ to ¾ of the length) adjacent the plate 10 and away from the part occupied by the plastics form 16, so that circulation of fluid around said form is not substantially hindered. The sleeve can be shrunk onto the helix by application of a hot air gun; but this can give rise to excessive shrinkage, thereby constricting the helix and making it difficult or impossible to insert a plastic form. It has been found that more consistent results can be obtained by immersing the helix and sleeve in very hot water. Alternatively, the sleeve may be moulded. Also, the sleeve may be attached to the plate 10.

As already described, the helix 14 may be fixed in the plate 10 by what, in use, is its upper end, as shown in FIGS. 1 and 2. Alternatively, the helix may be fixed in the plate 10 at an intermediate location along its length, e.g., at the location indicated by reference numeral 28 in FIG. 4. If desired, the sleeve 26 may be used in fixing the helix in the plate 10, and the sleeve may also be extended to the end 30 of the helix, for easier insertion of an object 16 in said helix. The sleeve need not then necessarily be shrunk on to the helix, but merely enclose it, since when it is in use it is above plate 10 and cannot slip off the helix.

Figure 5:
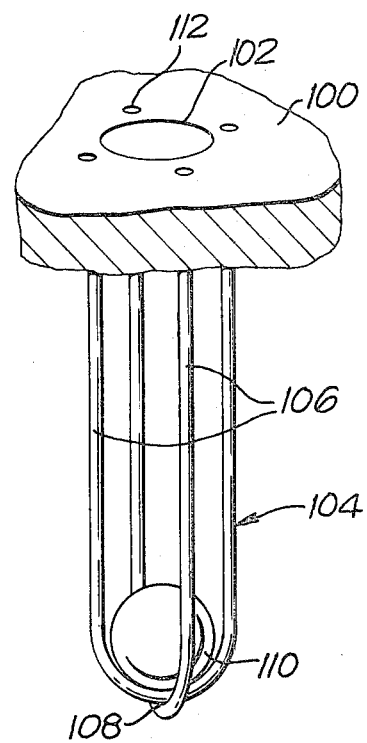
FIG. 5 illustrates a cage-like structure in the form of a basket.

A modified form of cage-like structure may be employed. Referring to FIG. 5, the planar member in the form of a plate is indicated by 100 and one of a number of holes therethrough, up to a hundred or more, is indicated by 102. The cage or basket, indicated generally by 104, is elongated, and extends from the plate normal thereto, and, in use, in a downward direction therefrom, as illustrated. The basket comprises four filaments 106 substantially parallel with one another over the greater part of their length, and mutually joined at 108, thereby supporting a spherical plastics form 110. The filaments 106 are fixed in the plate 100 by means of a close fit in bores, indicated by 112, in plate 100.

The filaments making up the cage 104 are made of a material which will not react with any liquid in which it is required to support the plastics forms 110. This may be done by making the filaments of a solid inert material or by covering a metal wire or other type of filament with an inert coating material.

Figure 6:
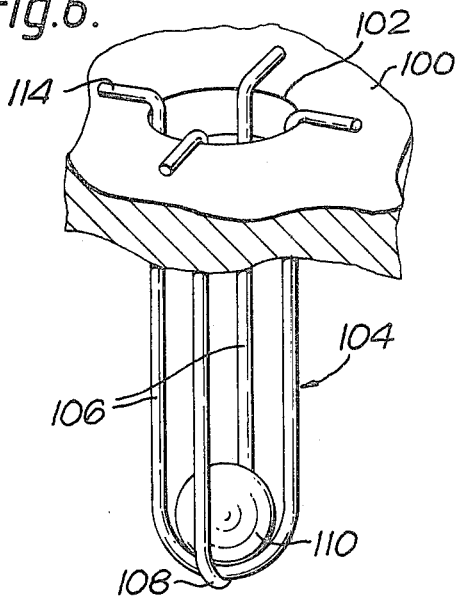
FIG. 6 illustrates a modified basket construction.

FIG. 6 illustrates an alternative way of fixing the basket 104 in the plate 100. Here the ends of the filaments 106 adjacent the plate 100 have an outwardly bent shape with end portions 114 substantially at right angles to the rest of the basket, so that they engage the upper surface of the plate 100, thereby preventing the basket from passing through the plate. This construction has the advantage that, if required, a basket can readily be removed from the plate 100.

Use of the support means is facilitated by constructing the cage-like structures, whether of helix—or basket-form, so as to be tapered in diameter away from the planar member, at least in the portion directly adjacent said member. This tapering facilitates the insertion of an array of cage-like structures into a corresponding array of containers, such as test tubes, without danger of one or more structures becoming fouled by an adjacent container.

Effective drainage of liquid from the support means, after immersion of a supported object, is desirable, in that it reduces contamination by one liquid of another in which the object may subsequently be immersed. It will usually be known what size and shape of object is to be held by the support means; a very common object being a spherical bead. Liquid tends to be retained between the object and the remote end of the cage-like structure, whether of helix—or basket-form. This retention is reduced by making said remote end conform substantially in shape, e.g., in radius of curvature, to the shape of the object, so that minimal gap exists between object and structure.

Controlling the speed at which the supported objects are withdrawn from immersion can also assist in reducing retention of liquid by the cage-like structures. The optimal withdrawal speed is in the order of 5 to 10 mm/sec.

Surface tension at the free surface of the liquid can be assisted to remove excess liquid by making the filament or filaments of the cage-like structures intersect the liquid surface at as steep an angle as possible. In the case of the helix-form, this involves using a steep helix angle, as steep as possible consistent with not permitting a supported object to escape laterally between turns of the helix. Such lateral escape can be avoided, while achieving a steep helix angle, by making the cage-like structure of two or more coaxial helices of the same diameter.

We claim:

1. An apparatus for supporting more than six reagent-coated objects during an analytical testing procedure in which the objects are immersed in a liquid analyte, comprising:

a substantially planar member having first and second planar surfaces parallel to one another, and having more than six siting means extending between said surfaces;

more than six elongated cage-like structures fixed to respective siting means and extending substantially perpendicularly downward from the planar member, said structures having a first end adjacent to the planar member and a second end remote from the planar member; each of said structures having a constriction at said second end, thereby retaining and supporting an object introduced to a siting means on the first surface side of the planar member and allowed to fall into the cage-like structure; and each of said structures having a shape at said second end corresponding to the shape of the object to be supported, thereby promoting drainage of the analyte liquid from the objects when the structures are removed from the liquid and, a reagent-coated, substantially spherically shaped object being located in each of said cage-like structures.

2. The apparatus of claim 1, wherein each cage-like structure comprises a basket-type structure consisting of a plurality of filaments.

3. The apparatus of claim 1, wherein the planar member is provided with locating holes having an unsymmetrical cross section, said holes being adapted to mate with pegs having a similar and complimentary cross section that are fixed to a coacting abutment whereon said planar member is locatable, whereby in use a planar member may only be associated with a corresponding abutment.

4. The apparatus of claim 1, wherein the planar member includes locating pegs having an unsymmetrical cross section, said pegs being adapted to mate with holes having a similar and complimentary cross section that are provided in a coacting abutment whereon said planar member is locatable, whereby in use a given planar member may only be associated with a corresponding abutment.

5. The apparatus of claim 1, wherein the planar member comprises a substantially flat plate and the siting means comprise holes in the plate.

6. The apparatus of claims 1 or 5, wherein the cage-like structures are tapered in diameter from the first end thereof toward the second end thereof.

7. The apparatus of claim 1, wherein each cage-like structure comprises at least one helix of filament-type material.

8. The apparatus of claim 7, wherein the helix is reinforced by an external sleeve of heat shrinkable material, said sleeve being shrunk around a portion of the helix in a manner such that circulation of the analyte liquid around the object supported in the second end of the helix is not substantially hindered.

9. The apparatus of claim 1, wherein each cage-like structure is constructed from a metal filament.

10. The apparatus of claim 9, wherein the metal is stainless steel.

11. The apparatus of claim 9, wherein the metal is covered with a layer of inert material.

* * * * *